United States Patent
Sarnow et al.

(10) Patent No.: US 9,642,593 B2
(45) Date of Patent: May 9, 2017

(54) SYSTEM AND METHOD FOR NON-INVASIVE DETERMINATION OF HUMAN BODY FAT

(71) Applicant: MuscleSound, LLC, Denver, CO (US)

(72) Inventors: Pierre Sarnow, Littleton, CO (US); Sean M McNamara, Denver, CO (US); Thomas M Moretto, Jr., Denver, CO (US)

(73) Assignee: MuscleSound, LLC, Denver, CO (US)

( * ) Notice: Subject to any disclaimer, the term of this patent is extended or adjusted under 35 U.S.C. 154(b) by 375 days.

(21) Appl. No.: 14/491,553

(22) Filed: Sep. 19, 2014

(65) Prior Publication Data

US 2016/0081654 A1    Mar. 24, 2016

(51) Int. Cl.
| G06K 9/00 | (2006.01) |
| A61B 8/08 | (2006.01) |
| A61B 5/00 | (2006.01) |
| A61B 8/00 | (2006.01) |

(52) U.S. Cl.
CPC .......... *A61B 8/0858* (2013.01); *A61B 5/4872* (2013.01); *A61B 8/4461* (2013.01); *A61B 8/5223* (2013.01)

(58) Field of Classification Search
None
See application file for complete search history.

(56) References Cited

U.S. PATENT DOCUMENTS

| 5,941,825 | A  | 8/1999  | Lang et al.     |
| 6,542,250 | B1 | 4/2003  | Michaelis et al. |
| 6,656,121 | B2 | 12/2003 | Jeong et al.    |
| 6,705,994 | B2 | 3/2004  | Vortman et al.  |
| 7,918,794 | B2 | 4/2011  | Pineau et al.   |
| 2003/0018257 | A1 | 1/2003 | Hsu et al.     |
| 2003/0144592 | A1 | 7/2003 | Jeong et al.   |

(Continued)

FOREIGN PATENT DOCUMENTS

NL    WO 2014115056 A1 *   7/2014    ........... A61B 8/0858

OTHER PUBLICATIONS

Dale R. Wagner, "Ultrasound as a Tool to Assess Body Fat," Journal of Obesity, vol. 2013, Article ID 280713, 9 pages, 2013. doi:10.1155/2013/280713.*

(Continued)

*Primary Examiner* — Hadi Akhavannik
(74) *Attorney, Agent, or Firm* — Brownstein Hyatt Farber Schreck, LLP

(57) ABSTRACT

Provided is a non-invasive system and method of determining human body fat based on image processing. The method includes receiving at least one ultrasound scan image of at least a portion of a skin layer as disposed above one or more additional tissue layers, the skin layer defining a horizontal axis and the image provided by a plurality of pixels. The method continues by horizontally blurring the pixels of the image and thresholding the pixels of the image to provide a binary image having a plurality of elements of different sizes. The method continues with morphing the structural elements of the binary image to remove small elements and connect large elements. With this resulting image, the method distinguishes a body fat layer from the remaining elements and determines the body fat layer thickness. An associated system is also disclosed.

46 Claims, 11 Drawing Sheets

(56) References Cited

U.S. PATENT DOCUMENTS

| | | |
|---|---|---|
| 2004/0006272 A1 | 1/2004 | Vortman et al. |
| 2006/0184024 A1 | 8/2006 | Da Silva et al. |
| 2007/0016061 A1 | 1/2007 | Da Silva et al. |
| 2007/0038092 A1 | 2/2007 | Jean-Claude et al. |
| 2009/0264756 A1 | 10/2009 | Da Silva et al. |
| 2009/0270728 A1 | 10/2009 | Da Silva et al. |
| 2010/0036246 A1 | 2/2010 | Kushculey et al. |
| 2012/0116223 A1 | 5/2012 | Da Silva et al. |
| 2012/0157842 A1 | 6/2012 | Davis et al. |
| 2013/0123629 A1 | 5/2013 | Rosenberg et al. |
| 2013/0289409 A1 | 10/2013 | Jeanne et al. |

OTHER PUBLICATIONS

Siobhan Leahy, Clodagh Toomey, Karen McCreesh, Cian O'Neill, Philip Jakeman, Ultrasound Measurement of Subcutaneous Adipose Tissue Thickness Accurately Predicts Total and Segmental Body Fat of Young Adults, Ultrasound in Medicine & Biology, vol. 38, Issue 1, Jan. 2012, pp. 28-34, ISSN 0301-5629, http://dx.doi.org/10.1016/j.ultrasmedbio.2011.*

Koda, M., Senda, M., Kamba, M. et al. Abdom Imaging (2007) 32: 387. doi:10.1007/s00261-006-9082-3.*

\* cited by examiner

SYSTEM AND METHOD FOR NON-INVASIVE DETERMINATION OF HUMAN BODY FAT

FIELD OF THE INVENTION

The present invention relates generally to the field of fitness and healthcare and more specifically to determination of glycogen stores in human tissue, and more specifically to the non-invasive determination of muscle glycogen stores.

BACKGROUND

The human body is composed of many types of tissues, not the least of which are bone, muscle, nervous, connective, circulatory and of course adipose tissue—more commonly known as body fat. For most people, the amount of certain types of tissues within the body, such as skeletal muscle and adipose tissue fat can be altered by choices in diet and exercise.

Although obesity is a growing problem in society at large, the reduction and elimination of all body fat is medically unsound. Indeed a healthy person will ideally have a balance of body fat, overall weight and lean tissue mass. Body Mass Index is also a widely recognized valuation of health and fitness and is often used and compared with body fat percentage in determining a variety of fitness and healthcare issues.

Indeed it has also been realized that muscle development and endurance is best established with yet again an ideal amount of body fat with respect to the person's weight and muscle mass.

Many methods of assessing a person's body fat and lean mass have been developed, such as but not limited to hydrostatic weighing, skin fold thickness measurements, and bioelectric impedance. But such methods have a number of drawbacks. Skinfold techniques involve an operator skillfully pinching the subject person's skin, without inducing pain, and measuring the thickens with a caliper. Moreover the operator must have reasonable skill in knowing how hard to pinch and where to pinch—factors that vary widely from one operator to another.

Hydrostatic weighing is perhaps the gold standard for determining body density and estimating body fat, and relies on the age old Archimedes' principle regarding the displacement of water by an object disposed in that water. Simply put, a person submerged in water will be buoyed by a counterforce equal to the weight of the water displaced. Muscle and bone are denser then water while fat is less dense—thus a person with a low percentage of body fat will have a higher body density and weigh more in the water then a person with a high percentage of body fat as weighed in the water.

But this process is not without issues. There must be estimation of pulmonary residual volume that may vary significantly from individual to individual, and even for an individual from one time to the next. High bone density also will tend to cause an underestimation of body fat while osteoporotic individuals are likely to see an overestimation. And of course hydrostatic testing requires a large facility, time and a person's willingness to get into the water.

X-ray and MRI imaging techniques may also be used, but of course there is a generally prevailing view that X-ray exposure should be limited so frequent use for body fat measurement may well provide more harm than benefit. And MRIs like hydrostatic testing require large facilities, time and willingness by the person to be placed into the system.

Ultrasound is an alternative form of body imaging which has shown some promise in a variety of areas including determining body fat. U.S. Pat. No. 5,941,825 to Lang et al. teaches a method involving at least two (2) different ultrasound pulses from two different locations and/or ultrasound devices having two (2) sources and two (2) detectors. With respect to both the Lang method and device, the difference in angle of the pulses is used to determine and reduce the parallax error. Of course this requires the ultrasound device to be properly positioned at the correct angle, which requires additional skill and training, or the use of a specialized device. In addition, it is noted that it is the signal that is analyzed for determination of body fat. Historical images or images that are generated principally for the imaging of other tissues are therefore not viable for processing as set forth by Lang.

U.S. Pat. No. 6,542,250 to Weber et al. provides a system for accurately measuring tissues thicknesses before, during and after a liposuction procedure which includes mapping adipose tissue thickness at key anatomical points. In one embodiment, the device comprises a remote control and data processing unit, a handheld ultrasound transducer, a monitor to display the information to the user and means to mark anatomical points of interest. Weber teaches, an ultrasound signal is transmitted into the tissue and the return signal collected. The collected signal is than communicated either through a direct wire connection or some wireless means, such as, RF, acoustic, or microwave to the remote control unit 20. The control unit 20 displays the recorded waveforms and calculated thickness of relevant layers. In addition, the control unit 20 stores the waveforms and information about the location of the measurement so that the user can easily monitor changes during the liposuction procedure. Again, this is strictly signal processing not image processing. Historical images or images that are generated principally for the imaging of other tissues are therefore not viable for processing as set forth by Weber.

Indeed there are a number of different US Application and Patents that have attempted to address the issue of determining body fat by ultrasound signal processing, and waveform analysis, but as noted with respect to Lang and Weber the reliance on signal processing or waveform processing is not the same as image processing and therefore entirely neglects both the possibility and the opportunity to use historical images or images that are generated principally for the imaging of other tissues.

Hence there is a need for a method and system that is capable of providing non-invasive determination of human body fat while overcoming the above identified challenges and or limitations.

SUMMARY

This invention provides a method and system for non-invasive determination of human body fat.

In particular, and by way of example only, according to one embodiment of the present invention, provided is a non-invasive method of determining subcutaneous human body fat, including: receiving at least one ultrasound scan image of at least a portion of a skin layer as disposed above one or more additional tissue layers, the skin layer defining a horizontal axis and the image provided by a plurality of pixels; horizontally blurring the pixels of the image; thresholding the pixels of the image to provide a binary image having a plurality of elements of different sizes; morphing the structural elements of the binary image to remove small elements and connect large elements; distinguishing a body fat layer from the remaining elements; and determining the body fat layer thickness.

In yet another embodiment, provided is a non-invasive method of determining subcutaneous human body fat, including: providing an ultrasound device having a movable transducer, the transducer operable in a high frequency range; selecting a target area of a subject; adjusting the ultrasound device for a depth of scan appropriate for the selected target area; disposing the transducer proximate to the subject and perpendicular to the selected target area; scanning the selected target area by processing ultrasound reflection received by the transducer to provide at least a partial scan image of the selected target area, the image provided by a plurality of pixels; horizontally blurring the pixels of the image; thresholding the pixels of the image to provide a binary image having a plurality of elements of different sizes; morphing the structural elements of the binary image to remove small elements and connect large elements; distinguishing a body fat layer from the remaining elements; and determining the body fat layer thickness.

Further, in yet another embodiment provided is a non-invasive system of determining human body fat, including: a processing unit; a memory storage device coupled to the processing unit; the processing unit being adapted to: receive at least one ultrasound scan image of at least a portion of a skin layer as disposed above one or more additional tissue layers, the skin layer defining a horizontal axis and the image provided by a plurality of pixels; horizontally blur the pixels of the image; threshold the pixels of the image to provide a binary image having a plurality of elements of different sizes; morph the structural elements of the binary image to remove small elements and connect large elements; distinguish a body fat layer from the remaining elements; and determine the body fat layer thickness.

Still, in yet another embodiment, provided is a non-transitory machine readable medium on which is stored a computer program comprising instructions to adapt a computer system having a processor to permit non-invasive determination of human body fat, the computer program including: a receiving routine operatively associated with an input device for receiving at least one ultrasound scan image of at least a portion of a skin layer as disposed above one or more additional tissue layers, the skin layer defining a horizontal axis and the image provided by a plurality of pixels; a horizontal blurring routine for horizontally blurring the pixels of the image; a thresholding routine for thresholding the pixels of the image to provide a binary image having a plurality of elements of different sizes; a morphing routine for morphing the structural elements of the binary image to remove small elements and connect large elements; and a distinguishing routine for distinguishing a body fat layer from the remaining elements and determining the body fat layer thickness.

BRIEF DESCRIPTION OF THE DRAWINGS

At least one method and system for non-invasive determination of human body fat will be described, by way of example in the detailed description below with particular reference to the accompanying drawings in which like numerals refer to like elements, and.

DETAILED DESCRIPTION

Before proceeding with the detailed description, it is to be appreciated that the present teaching is by way of example only, not by limitation. The concepts herein are not limited to use or application with a specific system or method for non-invasive determination of human body fat. Thus although the instrumentalities described herein are for the convenience of explanation shown and described with respect to exemplary embodiments, it will be understood and appreciated that the principles herein may be applied equally in other types of systems and methods involving the determination of body fat and specifically subcutaneous body fat in humans.

Figure 1:
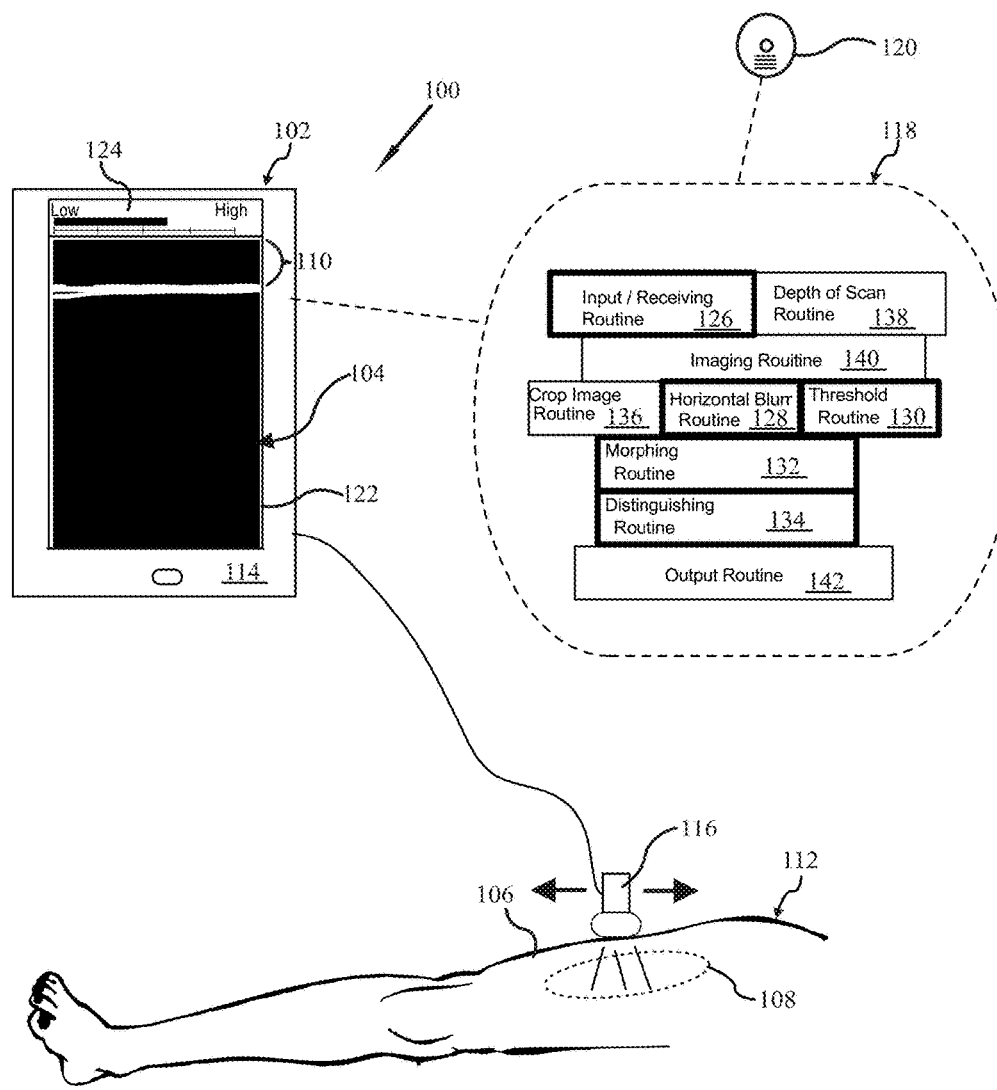
FIG. 1 illustrates a high level block diagram of a system for non-invasive determination of human body fat in accordance with at least one embodiment.

Turning to FIG. 1, presented is a high level block diagram of a system for non-invasive determination of adipose tissue, aka body fat (SNDBT) 100. For at least one embodiment SNDBT 100 is a body fat evaluator 102 structured and arranged to evaluate at least one selected portion of an ultrasound scan image that has undergone image processing, i.e. image 104 of at least a portion of a skin layer 106 disposed above one or more additional target tissues 108 to determine a measurement of body fat 110, and most specifically a measurement of the body fat as between the skin and muscle tissue of a subject 112.

As used herein, the term "skin" is understood and appreciated for it's normal meaning as is expected in the medical profession—namely, an ever changing organ that contains many specialized cells organized in three generalized layers—the epidermis, the dermis and subcutaneous tissue. Of course each of these layers may also be described as being comprised of multiple layers. With respect to the present invention and this description, the skin layer 106 is understood and appreciated to be one or more of the layers of epidermis, dermis and subcutaneous tissue. Precise identification and distinction of these layers is not necessary for most embodiments. Indeed the identification of the skin layer 106 serves generally as a point of reference in image 104. Moreover, in varying images, the skin layer 106 may be shown in an image as a portion of the subcutaneous tissue, a portion of the dermis and the subcutaneous tissue, and/or a portion of the epidermis and the dermis and the subcutaneous tissue.

As used herein the term "scan" is understood and appreciated for its normal meaning and as is expected in the medical profession—namely, "a. examination of the body or an organ or part, or a biologically active material, by means of a scanning technique such as ultrasonography—an ultrasound-based diagnostic imaging technique used for visualizing subcutaneous body structures; b. the image so obtained."

With respect to the present invention, and as is set forth in greater detail below and in the accompanying figures, the scan image is the element of importance. As such as used herein the terms "scan image," and or "image" are understood to be synonymous. Moreover, the ultrasound transducer provides a signal that for the present invention is rendered as an image comprised of a plurality of pixels. The present invention teaches the processing and evaluation of the resulting image, and not the processing, evaluation or transformation of the original ultrasound signal or waveform.

In at least one embodiment, SNDBT 100 has a processor-enabled device such as computer 114. Computer 114 is adapted to receive the information from the ultrasound transducer 116 and provide a scan image of a portion of a skin layer 106 disposed above one or more additional target tissues 108, of the subject 112. For illustrative purposes the portion shown of the subject 112 is that of the right leg, but as will be further discussed below, SNDBT 100 can, and for at least one embodiment is, applied to multiple different locations of the subject's body.

With respect to FIG. 1, SNDBT 100 is at least in part conceptually illustrated in the context of an embodiment for a computer program 118. Such a computer program 118 can be provided upon a non-transitory computer readable media, such as an optical disc 120 or RAM drive that can be provided to a computer 114 to be adapted as SNDBT 100. As is further shown and described in connection with FIGS. 10-13, in alternative embodiments the computer program 118 can be provided to a computer serving at least as part of an application providing platform, such as but not limited to the Apple App Store, that platform in turn operable to provide the computer program 118 to a computer 114 to be adapted as SNDBT 100.

As will be discussed further below, SNDBT 100 may be employed upon a computer 114 having typical components such as a processor, memory, storage devices and input and output devices. During operation, the SNDBT 100 may be maintained in active memory for enhanced speed and efficiency. In addition, SNDBT 100 may also be operated within a computer network and may utilize distributed resources.

In at least one embodiment, the SNDBT 100 system is provided as a dedicated system to provide non-invasive determination of body fat. In at least one alternative embodiment, the SNDBT 100 system is achieved by adapting an existing computer 114 such as a smart phone (such as an iPhone® or Android®) or tablet computer (such as an iPad®) which is portable.

With respect to FIG. 1, SNDBT 100 has been conceptually illustrated as a tablet computer 114, having a display 122 operable to display a visual representation of the scan image 104. The display 122 also is shown to provide an indicator 124 to inform an operator of the determined body fat thickness.

For at least one embodiment, the software may be described as including an input/receiving routine 126, a horizontal blurring routine 128, a threshold routine 130, a morphing routine 132, and a distinguishing routine 134. As is set forth and described below, the elements of SNDBT 100 may be summarized or at least one embodiment as follows.

The input/receiving routine 126 is operatively associated with an input devices to receive the scan, such as a Digital Imaging and Communications in Medicine (DICOM) data file, and may also receive other information such as the subject's name, location, current state of exertion, etc. . . . . . If not in image form, this received scan is provided to the operator as a scan image 104 comprised of a plurality of pixels. The horizontal blurring routine 128 is operable to horizontally blur the pixels of the image. The thresholding routine 130 is operable to threshold each pixel to provide a binary image having a plurality of elements of different sizes. The morphing routine 132 is operable to morph elements of the processed image to remove small elements and connect large elements. The distinguishing routine 134 is operable to distinguish a body fat layer from the remaining elements and determine the body fat layer thickness.

For at least one embodiment, SNDBT 100 may also include an optional cropping routine 136. As has been noted above and will be further understood and appreciated with respect to the following description, the present invention advantageously is distinguishing a subject's body fat layer through image processing. More specifically image processing techniques including blurring, thresholding, and morphing are advantageously combined so as to process a scan image and provide processed image 104 in such a way as to quickly and very accurately distinguish body fat thickness.

In this respect, for at least one embodiment between $\frac{1}{10}^{th}$ and $\frac{1}{5}^{th}$ of the image is vertically cropped from one or both sides so as to leave a more central portion of the original scan image for subsequent image processing. For at least one alternative embodiment, no cropping is performed.

In addition to the core routines, input/receiving routine 126, a horizontal blurring routine 128, a threshold routine 130, a morphing routine 132, and a distinguishing routine 134, in at least one alternative embodiment, SNDBT 100 further includes an ultrasound device having a movable transducer 116 operable in a high frequency range and has an adjustable depth of scan. More specifically, the high frequency range is between about 5 to 20 megahertz. In addition the depth of scan is between about 1 centimeter and about 7 centimeters. For at least one embodiment, the ultrasound transducer 116 is an existing commercially available and FDA approved ultrasound transducer 116 incorporated as part of SNDBT 100 without departing from the scope of FDA approval for the operation of the ultrasound transducer device.

For at least one embodiment of SNDBT 100, the computer program 118 may additionally include a depth of scan routine 138, an imaging routine 140, and optionally an output routine 142. Moreover, the depth of scan selector routine 138 is operable to adjust the ultrasound device, e.g., ultrasound transducer 116, for a depth of scan appropriate for the target tissues 108. In at least one embodiment, the proper depth of scan is set based on the selection of a target tissues 108 as indicated by an operator of SNDBT 100.

The imaging routine 140 is operable to direct the movable transducer 116 to scan the selected target tissues 108 by processing ultrasound reflection received by the transducer to provide at least a partial ultrasound scan of the selected target muscle. In at least one embodiment, the imaging routine 140 is structured and arranged to operate with a third party ultrasound imaging software provided to the computer 114.

For at least one embodiment, the optional output routine 142 is operable to output the scan of the target tissues 108 to a storage device, or database. This output routine may also be configured to provide an audible, visual or tactile output to inform the operator of SNDBT 100 of the determined body fat layer thickness.

With respect to FIG. 1, it is understood and appreciated that the elements, e.g., input/receiving routine 126, horizontal blurring routine 128, threshold routine 130, morphing routine 132, distinguishing routine 134, crop image routine 136, depth of scan routine 138, imaging routine 140, output routine 142 ultrasound transducer 116 and computer 114 are in at least one embodiment located within a single device. In at least one alternative embodiment, these elements may be distributed over a plurality of interconnected devices. Further, although each of these elements has been shown conceptually as an element, it is understood and appreciated that in varying embodiments, each element may be further subdivided and/or integrated with one or more other elements.

Figure 2:
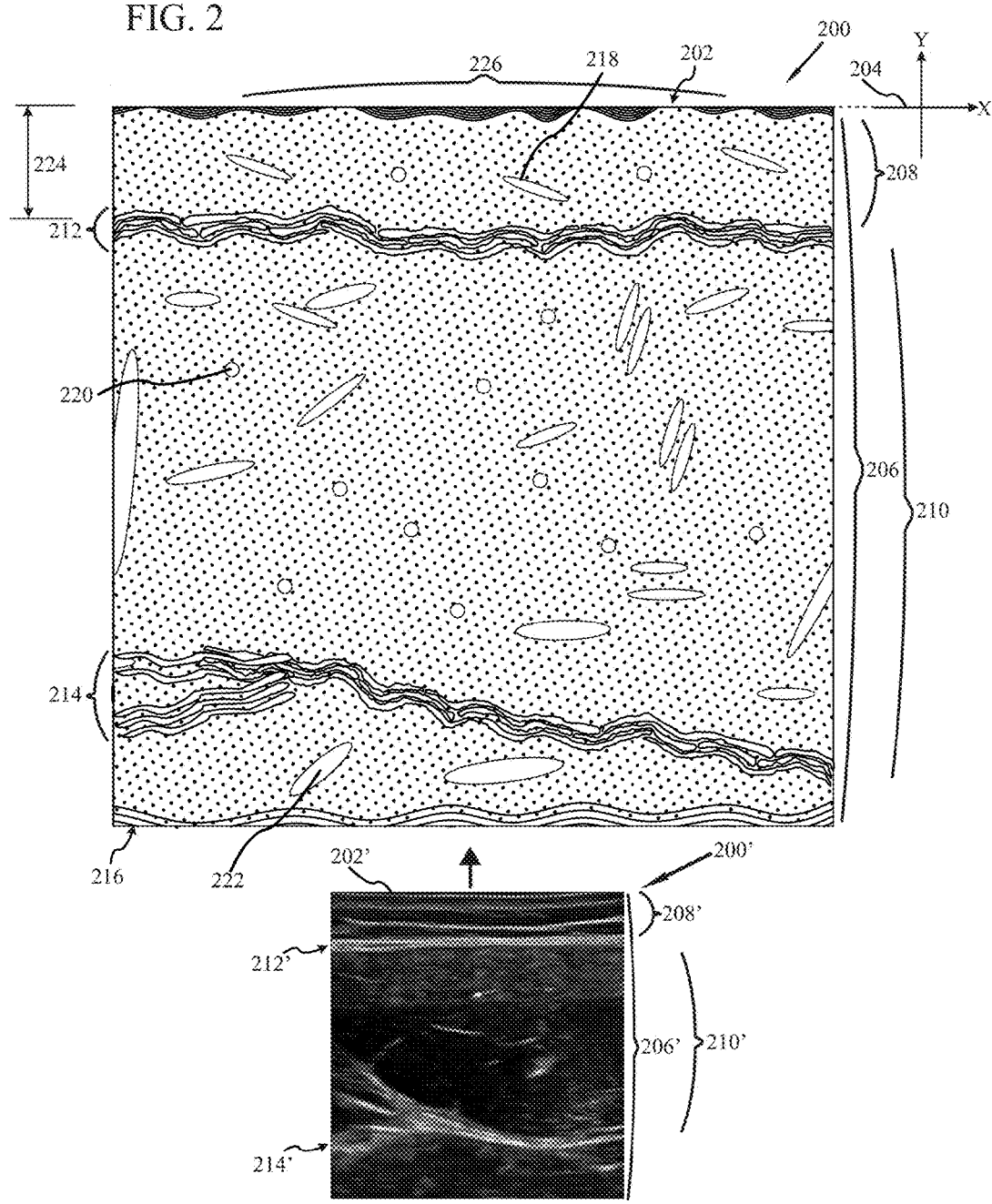
FIG. 2 is a conceptual illustration of an ultrasound scan of target tissues in accordance with at least one embodiment.
Figure 3:
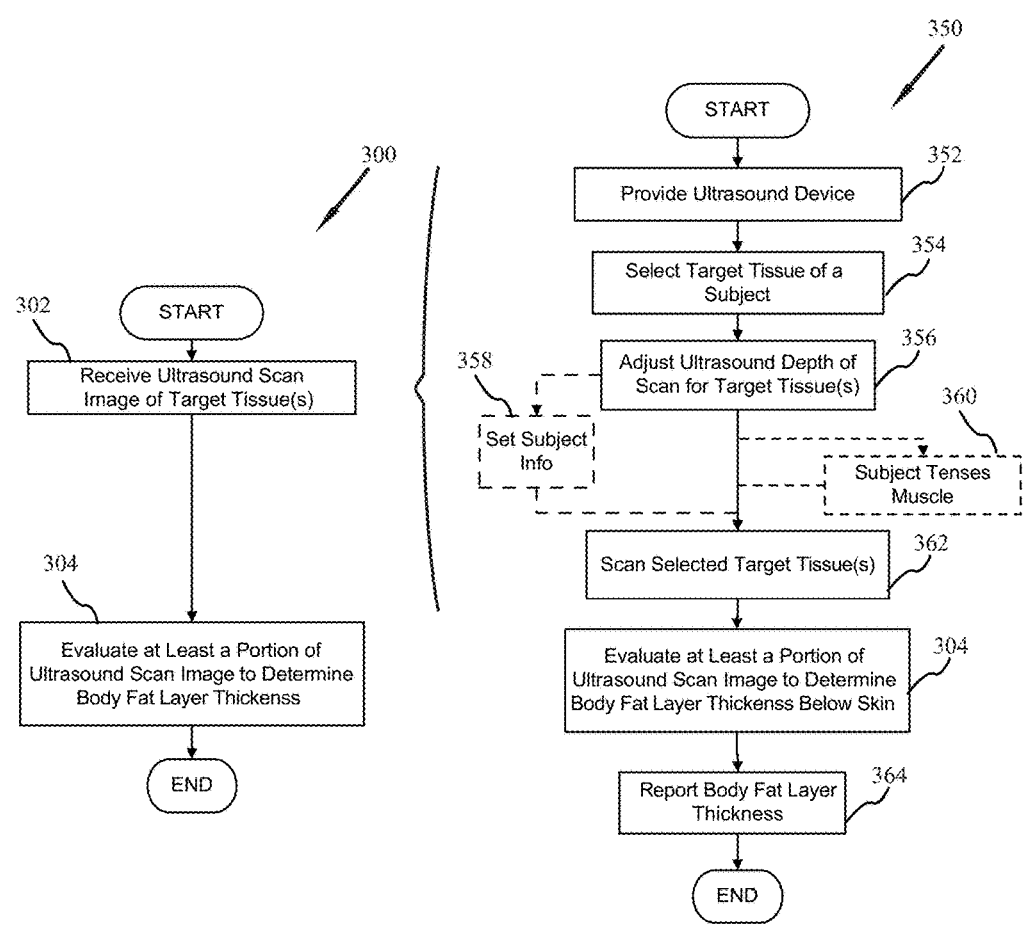
FIG. 3 is a high level flow diagram for a method of non non-invasive determination of human body fat in accordance with at least one embodiment.
Figure 4:
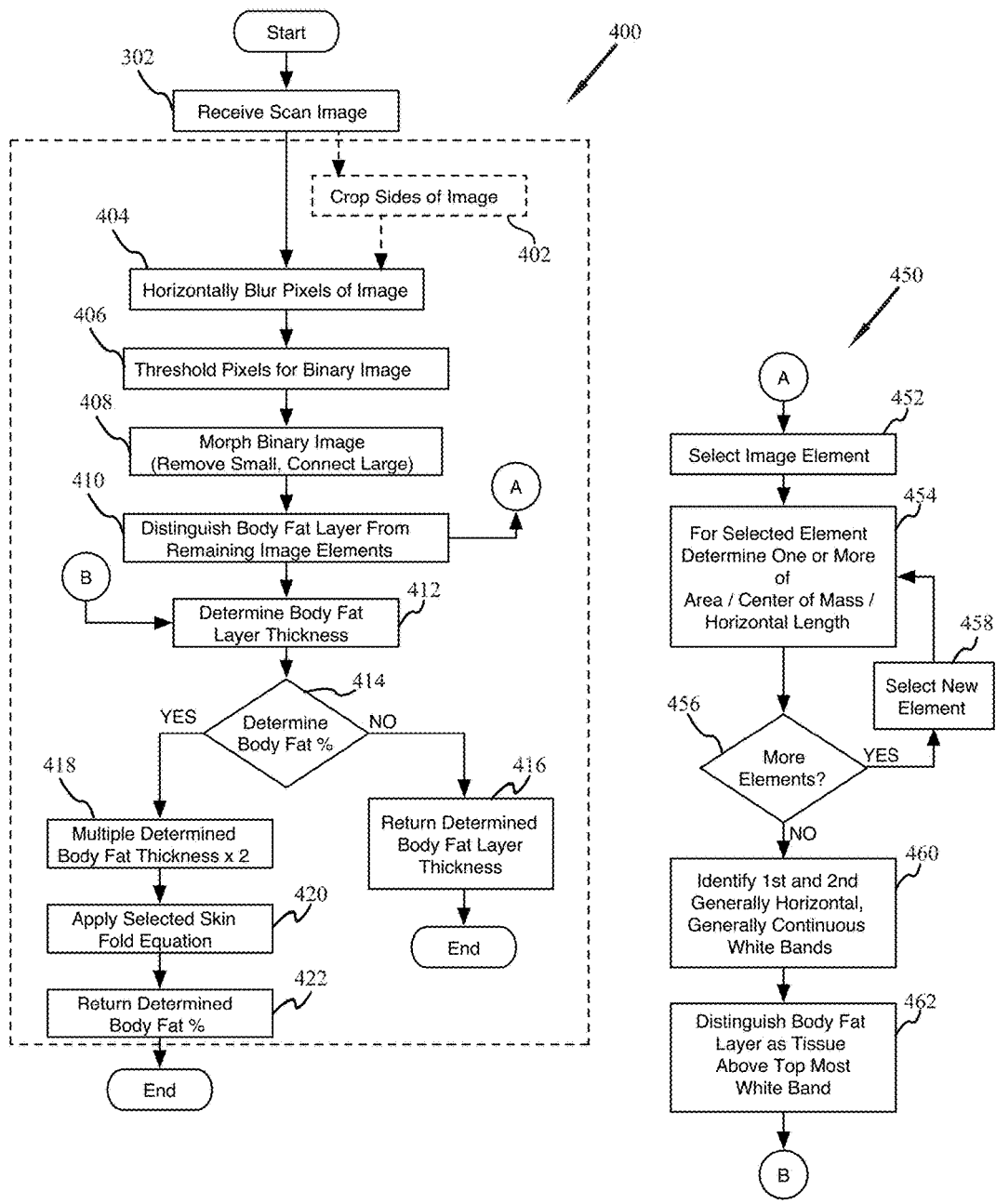
FIG. 4 is a refined flow diagram for the evaluating operation for non-invasive determination of human body fat in accordance with at least one embodiment.

FIGS. 3 and 4 in connection with FIGS. 1, 2 and 5-9 provide a high level flow diagram with conceptual illustrations depicting a method 300 for non-invasive determination of human body fat in accordance with at least one embodiment. It will be appreciated that the described method(s) need not be performed in the order in which it is herein described, but that this description is merely exemplary of one method of non-invasive determination of human body fat stores.

As is shown in FIG. 2, an enlarged conceptual ultrasound scan image 200 is shown corresponding to a real ultrasound scan image 200'. Typically ultrasound scan images such as scan image 200' are rendered in black and white in accordance with a grey scale, though color is certainly an option and within the scope of the present invention. Various structures with a subject's body reflect the ultrasound signal with varying intensity. In general there are two distinct patterns of reflection that give rise to the echoes that make up the ultrasound image—specular reflections and scattering reflections.

Specular reflections are responsible for the bright appearances of fibrous structures such as tendons, ligaments and the boundaries between different types of tissues. Scattering gives rise to the characteristic texture of an image seen within soft tissues. The scan image 200' is composed of a plurality of pixels. Scan pixels may correlate directly with image pixels as used to render scan image 200. Of course, in some embodiments the resolution of the scan pixels may be greater then the resolution applied in the scan image, such that each pixel of the scan image may correlate to two or more pixels of the scan.

Those skilled in the art of ultrasound imaging can and often do perceive a great deal of information from images that are otherwise perhaps visually interesting but also perhaps largely unintelligible to the untrained eye.

Through image processing as performed by SNDBT 100 and method 300, this training to perceive and differentiate structures within a typical ultrasound image is for all intensive purposes eliminated. For ease of discussion, conceptual rendering of ultrasound images has been provided to ease and facilitate this discussion.

Moreover, as shown in FIG. 2, the scan image 200 may capture a portion of the surface tissue 202, such as the skin at the top of the images, which defines a horizontal axis 204 for the scan image 200. The scan image 200 also shows at least a portion of subcutaneous tissues 206, which likely includes an as yet not clearly delineated area of body fat tissue 208, muscle tissue 210 and other tissues such as fibrous tissues 212 and 214, bone tissue 216 and other tissues, of which 218, 220 and 222 are exemplary. This same variety of tissues is of course evident in real ultrasound scan image 202', a subset of which have been suggestively identified with like numbers 202', 206'-214'.

Moreover, although scan image 200 provides enough information to discern the presence of body fat tissue 208, muscle tissue 210 and other tissues, these tissues are not sufficiently distinguished so as to permit accurate determination of body fat tissue thickness at this point. Indeed, embodiments of the present invention advantageously apply image processing techniques so as to cleanly distinguish at least the body fat tissue 208 to such a degree that a highly accurate thickness measurement may be obtained.

As noted above and further described below, for at least one embodiment between $\frac{1}{10}^{th}$ and $\frac{1}{5}^{th}$ of the image is vertically cropped from one or both sides so as to leave a more central portion 226 of the scan image 200 for subsequent image processing. This cropping is more fully illustrated with respect to FIG. 5.

Further, although the illustrations and discussion provided herein for exemplary purposes generally appear to be 2D (two dimensional) images, the system and methods are equally applicable multi-axis ultrasound imaging techniques, such as for example 3D ultrasound.

FIG. 3 provides a high level flow diagram depicting a method 300 for non-invasive determination of body fat, which is more fully appreciated with respect to FIGS. 2 and 5-9 providing both real and conceptual illustrations of ultrasound scan images as processed in accordance with at least one embodiment. It will be appreciated that the described method, as well as all other subsequent methods and refinements to the disclosed methods need not be performed in the order in which they are herein described, but that the descriptions are merely exemplary of a method or methods that could be performed for non-invasive body fat determination.

As shown in FIG. 3, in general method 300 commences with receiving an ultrasound scan image of target tissue(s), block 302. An exemplary scan image such as scan image 200 is shown in FIG. 2. Moreover, even though body fat may be the primary tissue of interest in one setting, for the body fat layer to be accurately determined under the present invention it is desirable to distinguish the body fat layer of tissue from other tissues. In addition, as the subcutaneous body fat layer is captured in ultrasound scans often performed with an intent to image a deeper tissue, such scan images may also be processed under the present invention for about real time or later analysis of body fat. Indeed, substantially real time analysis to determine a subject's body fat tissue thickness may be performed as a specific procedure, or as a beneficial ancillary procedure when a subject is undergoing an ultrasound imaging process for another purpose.

Moreover, scan image 200 may be provided as described above through the use of SNDBT 100 in an embodiment providing an ultrasound transducer 116, or through another ultrasound imaging system and or process. For at least one embodiment the ultrasound scan image is provided by the system(s) and methods as set forth in U.S. Pat. No. 8,562,529 entitled Method and System for Non-Invasive Determination of Glycogen Stores, U.S. Pat. No. 8,517,942 entitled Method for Non-Invasive Determination of Glycogen Stores, U.S. Pat. No. 8,512,247 entitled System for Non-Invasive Determination of Glycogen Stores, and U.S. patent application Ser. No. 14/012,538 entitled System and Method for Target Muscle Glycogen Score Determination and Evaluation—each of which is incorporated herein by reference.

With the scan image 200 now received, method 300 continues with the evaluation of at least a portion of the scan image 200 to determine body fat layer thickness, block 304. For application of method 300, an embodiment of SNDBT 100 need not have, or otherwise be coupled to, an ultrasound transducer 116. Method 300 may also be performed by SNDBT 100 when a user desires to review historical data of tissue scans, such as for example to revisit past histories of evaluation to perceive changes in development and potential adjustments to a subject's training methods, general activities, diet or other form of activity and/or medication.

Of course, for real time non-invasive determination of body fat, in varying embodiments SNDBT 100 may indeed include an ultrasound transducer 116 as described above. As such, method 300 may be augmented as method 350, the augmentation as illustrated pertaining to at least one method of providing the received ultrasound scan image 200.

More specifically, for augmented method 350, an ultrasound transducer 116 is provided as part of SNDBT 100, block 352. A target tissue, such as a muscle known to be below the subcutaneous body fat tissue, e.g. target tissue(s) 108, is selected, block 354. As noted, the ultrasound transducer has an adjustable depth for scanning, such as a selection between about 0.5 and 10 centimeters. The ultrasound transducer 116 is adjusted to provide a depth of scan appropriate for the selected target tissue, block 356.

In at least one embodiment, the depth of scan is adjusted manually, such as to about 3.5 centimeters for the skin, body fat and rectus femoris muscle. In an alternative embodiment, the depth of scan is automatically selected by an operator selecting a desired tissue, such as a muscle tissue, e.g., rectus femoris, vastus lateralis, or biceps. In addition, in varying embodiment, the auto-determined and set depth may also be adjustable by the operator so as to permit adjustment for various body types.

In at least one embodiment additional and optional information about the subject is recorded, as indicated by dotted block 358. This optional information may include, but is not limited to, details such as the subject's name, age, gender, time of day, status of subject—at rest/at VOT Max, after eating, or other such information desired to be recorded and displayed in connection with the scanned image of the target muscle.

Moreover, to summarize for at least one embodiment, the augmented method 350 includes providing an ultrasound device having a movable transducer, the transducer operable in a high frequency range, selecting a target tissue 108 of a subject 112 and adjusting the ultrasound device for a depth of scan appropriate for the selected target tissue 108.

As the ultrasound transducer 116 operates by providing a high frequency signal that is directed into tissue and detecting reflections returned by encountered elements, it is understood and appreciated that the transducer should be aligned generally perpendicular to the selected target muscle. Of course, if a transducer having an alignment configuration that is other than perpendicular is employed the specific alignment as intended for the transducer should be used.

It is understood and appreciated that an ultrasound transducer 116 may be positioned along the longitudinal or latitudinal axis of the tissue or somewhere in between. For general alignment purposes and ease of operation, in general the operator of the system will select ultrasound transducer 116 alignment matching to either the longitudinal or latitudinal axis of the target tissue 108.

Testing has determined that a key factor for deciding which alignment to use is perhaps the initial quality of the scan image. In other words, for at least one embodiment, at least a longitudinal and a latitudinal image of the target tissues is obtained so that the images can be compared by the operator or SNDBT 100 to determine which image is best for analysis.

Application of the ultrasound transducer 116 against the subject's skin can be a practiced skill, for if too much pressure is applied the transducer may inadvertently compress the tissue and thereby hamper the quality of the scan and the resulting evaluation of body fat tissue thickness. However, an easy solution presents itself that substantially minimizes the risk of transducer related compression of the tissue.

As shown by optional dotted block 360, the subject can simply tense his or her muscle if it is the target tissue 108 or directly below the target tissue. More specifically, if the subject acts to tense his or her muscles adjacent to the desired target tissue, the natural action of the muscle contraction causes the muscle to swell and thereby resist compression. The contracted and thereby enlarged muscle may also be advantageous in providing an even clearer cross sectional scan then may be obtained with a relaxed muscle.

In short, while the quality of the scan for the tensed or un-tensed muscle adjacent to the target tissue 108 may be the same for an operator skilled in how much pressure to apply, for the novice, as well as the skilled operator, tensing an adjacent muscle does not appear to significantly hamper the determination of body fat tissue thickness may help insure greater consistency of scans in a wide variety of locations and settings. Indeed, for at least one embodiment, when the method of scanning a target tissue(s) 108 is performed, the subject will tense his or her adjacent muscle as a normal and expected part of the scanning process.

Moreover, to achieve the scan of the target tissue 108, the ultrasound transducer 116 is disposed proximate to the target tissue and as the ultrasound transducer 116 is activated the target tissue(s) 108 is scanned, block 362. In at least one embodiment the ultrasound transducer 116 is placed in direct contact with the subject's skin. In at least one alternative embodiment, a protective cover, shield or even the subject's clothing is disposed between the ultrasound transducer 116 and the subject's skin.

A scan image is then provided from the resulting scan, and evaluated as noted above, block 304. A report of the determined body fat layer thickness may also be reported, block 364

In other words, to summarize for at least one embodiment, the augmented method 350 continues with disposing the transducer proximate to the subject 112 and perpendicular to the selected target tissue 108, and then imaging the selected target tissue 108 by processing ultrasound reflection received by the transducer to provide at least a partial scan of the selected target tissue 108. Many ultrasound transducers provide images as cross sections of the tissues and structures whereas others may provide 3-D views. For consistency in analysis, in at least one embodiment the operator of SNDBT 100 adopts a convention to scan a target tissue along its long axis or short axis.

For the majority of leg and arm tissues the long axis is generally parallel to bone structure and the short axis is generally perpendicular to bone structure. Indeed in some embodiments, scans with SNDBT 100 may be performed substantially contemporaneously along both the long and short axis of a target tissue 108 for enhanced comparison and analysis.

Method 350 then continues with the evaluation of the scan as discussed above with respect to block 304. For at least one embodiment, it is understood and appreciated that the evaluation of the scan 104 is performed about contemporaneously with the scanning of the target tissue 106.

The determined body fat tissue thickness 222 is then reported to the operator, block 364. The determined body fat tissue thickness may also be recorded for use in plotting the changes in a subject's body fat store over time, and or in response to various different points of exercise, conditioning, diet, medication and other factors.

FIG. 4 in connection with FIGS. 5-9 provides a high level flow diagram with conceptual illustrations to further refine at least one embodiment of method 300 for evaluating at least a portion of the ultrasound scan image to determine body fat layer thickness. Moreover in FIG. 4, method 400 corresponds in greater detail to block 304 of FIG. 3. Again, it is appreciated that the described method need not be performed in the order in which it is herein described, but that this description is merely exemplary of one method for non-invasive determination of human body fat thickness.

More specifically, as FIG. 4 expands on FIG. 3, initially a scan image of the target tissues 108 is received, block 302. An exemplary image scan is conveniently provided as scan image 200 as shown and described above with respect to FIG. 2.

Figure 5:
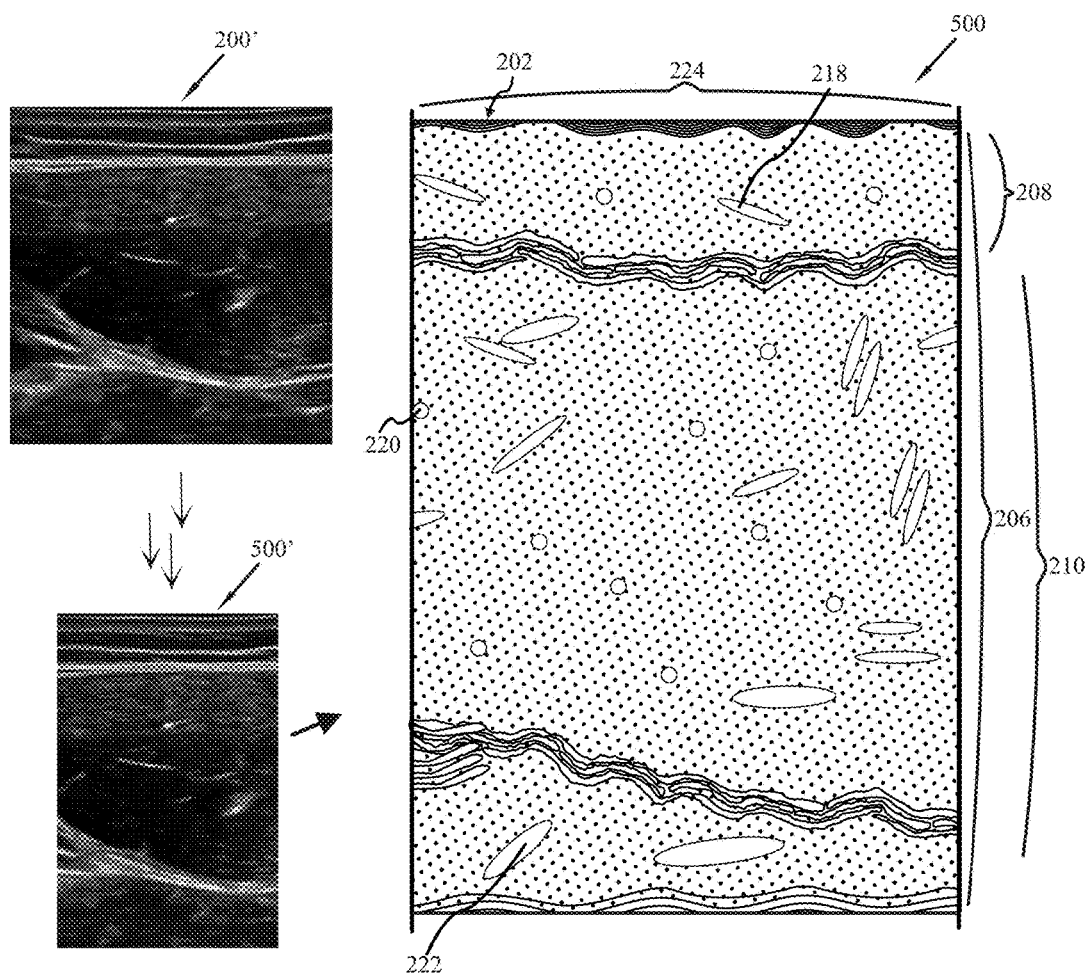
FIG. 5 is a conceptual illustration of a cropped ultrasound scan image in accordance with at least one embodiment.

Ultrasound scan images tend to image tissues directly below the transducer most clearly, with the side areas of the scan tending to be less clear. For purposes of subsequent image enhancement, for at least one embodiment one or both sides of the scan image 200 are cropped as is shown in FIG. 5 as cropped scan image 500. Moreover, cropped image 500 is the more central portion 226 of scan image 200 shown in FIG. 2. Although embodiments of method 300 may be performed without side cropping, in general between 1/10 and 1/5 of the image is vertically cropped from each side as suggested by dotted lines and optional block 402.

With respect to FIG. 5, as with FIG. 2 above the conceptual cropped scan image 500 is shown to generally corresponding to real cropped ultrasound scan image 500'.

Figure 6:
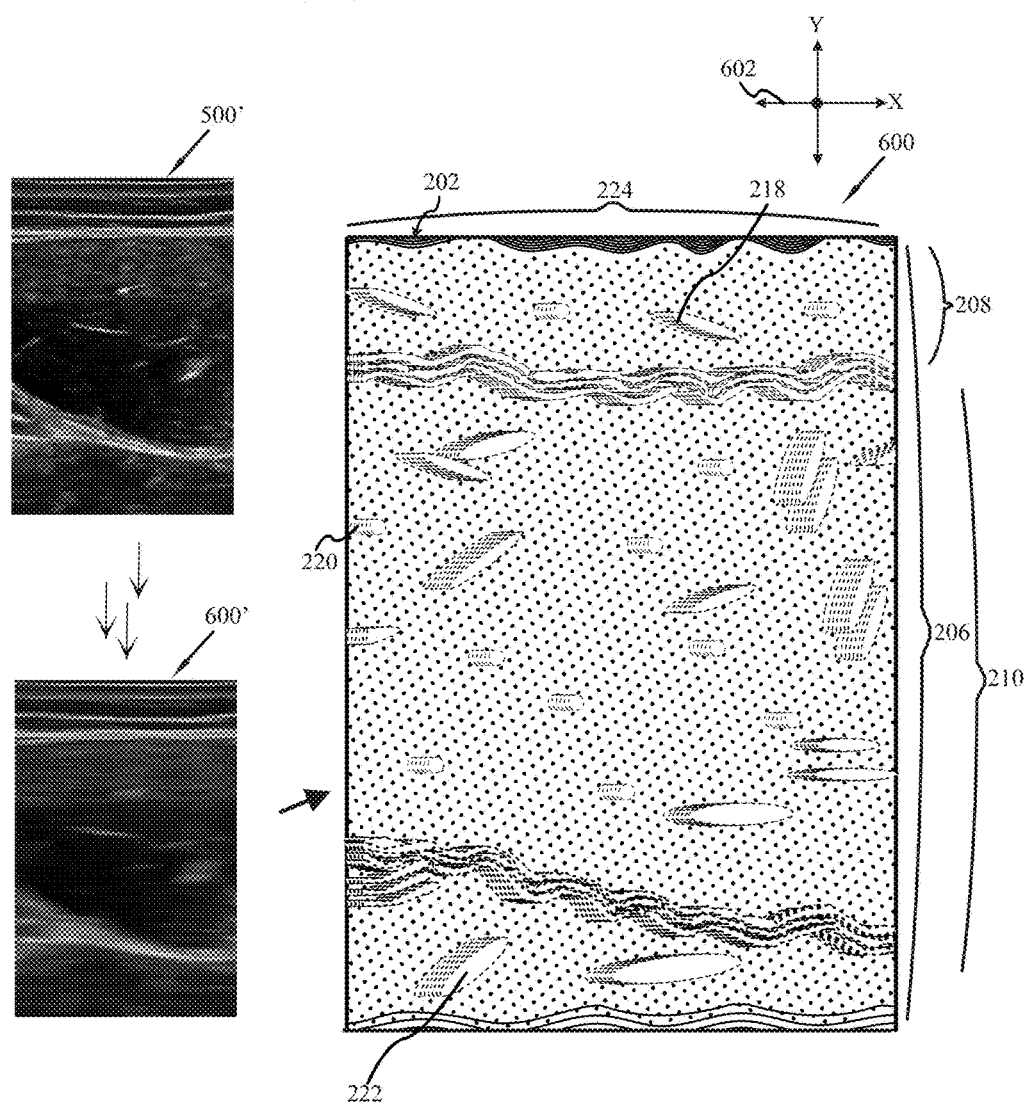
FIG. 6 is a conceptual illustration of a horizontally blurred ultrasound scan image in accordance with at least one embodiment.

Next, method 400 proceeds to horizontally blur the pixels as shown in the horizontally blurred scan image 600 shown in FIG. 6, block 404 (see FIG. 4). Again blurred scan image 600 conceptualizes blurred real ultrasound scan image 600'.

Traditionally the clarity of an ultrasound image and indeed the sharpness of the elements within the ultrasound image are very important. This is quite understandable as often times an ultrasound image is used to guide a doctor in the ablation of adipose tissues so clear imaging is important for both the doctor and the patient.

For the present invention, sharpness of detail within the image is not important. In fact, the present invention advantageously teaches how image processing techniques are applied so as to remove elements of small detail so as to enhance the ultimate distinguishing of body fat thickness. In image processing, a kernel such as a convolution matrix, mask or filter is a small matrix that can be applied to propagate a change in a source image for a desired effect. Moreover the change imparted is a result of convolution between an applied kernel and an image.

Blurring is an image processing technique commonly applied so as to reduce noise and reduce detail. Blurring functions are well understood and known to those skilled in the art and need not be discussed in detail here.

A high level discussion of blurring is provided so as to facilitate general understanding of the process so as to further appreciate the advantageous achievement of SNDBT 100 and method 300. In simple terms blurring an object means that each of the pixels in the source image gets spread over and mixed with surrounding pixels. With respect to the present invention, blurring may be achieved by application of a Mean Filter, Weighted Average Filter, Gaussian Filter or other appropriate filter. A Mean Filter is also known as Box Filter or Average Filter, and is understood to have the following properties—it is odd ordered, the sum of all elements should be 1 and the elements of the filter are the same. A Weighted Average Filter acts as the name implies—giving more weight to the center value. Here again it is odd ordered, the sum of all elements should be 1, but the weight of the center element should be more than all of the other elements. A Gaussian Filter is one that uses a Gaussian function, which also expresses the normal distribution in statistics, for calculating the transformation to apply to each pixel in the image.

For purposes of the present invention, blurring is only to be applied along the horizontal axis. As such a 1×3 Mean Filter or a one dimension Gaussian Function is typically appropriate. For at least one embodiment, the blurring filter is a 1 dimensional Gaussian function:

$$G(x) = \frac{1}{\sqrt{2\Pi\sigma^2}} e^{-\frac{x^2}{2\sigma^2}}$$

For at least one alternative embodiment, a 1×3 Mean Filter such as [1/3, 1/3, 1/3] is applied.

As is shown in FIG. 6, in conceptually blurred image 600, the tissue elements such as 222 and 224 have been blurred along the horizontal X axis as indicated by coordinate axis 602. No blurring has occurred along the vertical Y axis. As such the edge distinctions along the horizontal axis are less sharp as blurring makes the collections of similar pixels either bigger or smaller. And again, conceptual blurred image 600 corresponds generally to actual blurred image 600'.

Figure 7:
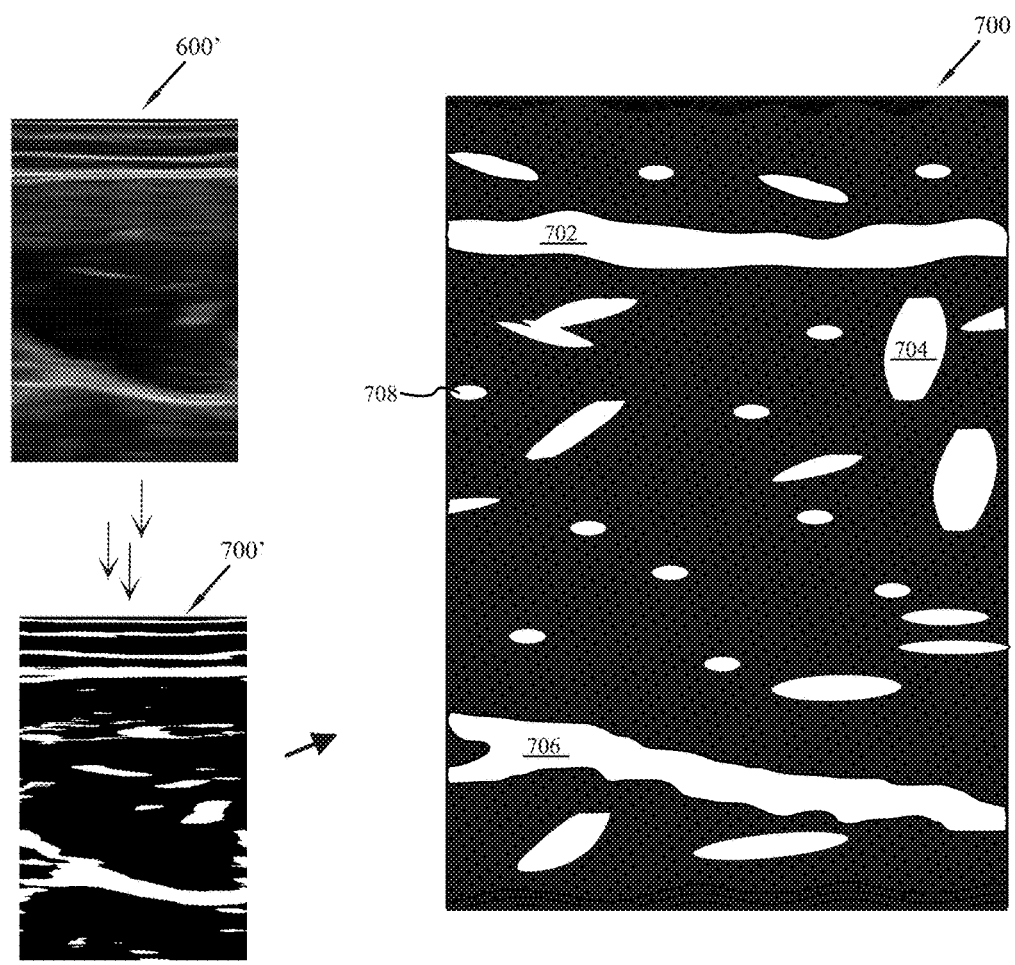
FIG. 7 is a conceptual illustration of a thresholded horizontally blurred image to provide a binary image in accordance with at least one embodiment.

Next, method 400 proceeds to threshold the pixels of the blurred image 600 to either black or white to provide a binary image 700, block 406, as shown in FIG. 7. Conceptual binary image 700 corresponds generally to actual binary image 700'.

Thresholding is a method of image segmentation and is well known to those skilled in the art and need not be discussed in detail herein. A high level discussion of thresholding is provided so as to facilitate general understanding of the process so as to further appreciate the advantageous achievement of SNDBT 100 and method 300. From a gray scale image, thresholding may be used to create binary image, such as binary image 700 from blurred image 600.

More specifically, each pixel of the blurred image 600 has a value equal to or ranging from black (i.e., 0) to white (i.e., 10). To threshold the pixels those above the midpoint of 5 are reset to 10 while those pixels at or below the midpoint of 5 are reset to 0. Of course this scale is merely exemplary and an alternative scale may be used. In addition, although color is the attribute for thresholding as described herein, in alternative embodiments thresholding may be applied to another color, luminance, darkness, contrast or other identifiable attribute of each pixel.

Moreover the present invention is further processing the scan image so as to provide a binary image has only two possible values for each pixel. The remaining elements, of which elements 702, 704, 706 and 708 are exemplary, are crisp white elements with very discernable edges.

Next, method 400 proceeds to morph the remaining elements of the binary image 700 to remove small elements and connect large elements. To "morph" or "morphing" refers to mathematical morphology—a technique for the analysis and processing of geometric structures based on set theory, lattice theory, topology and or random functions and is a known technique applied to digital images. The basic morphological operators or morphological functions as they are also known are erosion, dilation, opening and closing. These morphological functions are well known to those skilled in the art and need not be discussed in detail herein.

A high level discussion of morphing, a.k.a. mathematical morphology, is provided so as to facilitate general understanding of the process so as to further appreciate the advantageous achievement of SNDBT 100 and method 300.

The basic idea in binary morphology of a binary image is it to probe an image with a simple, predefined shape such as a disc, square, cross or other simple geometric shape which is referred to as a structuring element and is itself a binary image. Opening removes white "holes" while closing removes black "holes." In accordance with at least one embodiment, the morphological function applied to further process the scan image so as to distinguish the body fat tissue thickness is the morphological function of opening.

Opening is obtained by eroding an image following by then dilating the image. The erosion of a binary image A (the binary image 700) by the structuring element B (a disc of radius r) in Euclidean space $E=R^d$ is generally understood by the equation:

$$A \ominus B = \{z \in E | B_z \subseteq A\}$$

where Bz is the translation of B by the vector Z, i.e.:

$$B_z = \{b+z | b \in B\}, \forall z \in E$$

When the structuring element B such as a square or disc has a center located on the origin E, the erosion of A by B can be understood as the locus of points reached by the center of B when B moves inside A.

The erosion of A by B is also given by the expression:

$$A \ominus B = \cap_{b \in B} A_{-b}$$

The dilation of A by the structuring element B is defined by:

$$A \oplus B = \cup_{b \in B} A_b$$

The dilation is commutative, also given by:

$$A \oplus B = B \oplus A = \cup_{a \in A} B_a$$

As before, when the structuring element B such as a square or disc has a center located on the origin E, the dilation of A by B can be understood as the locus of the points covered when the center of B moves inside A.

Figure 8:
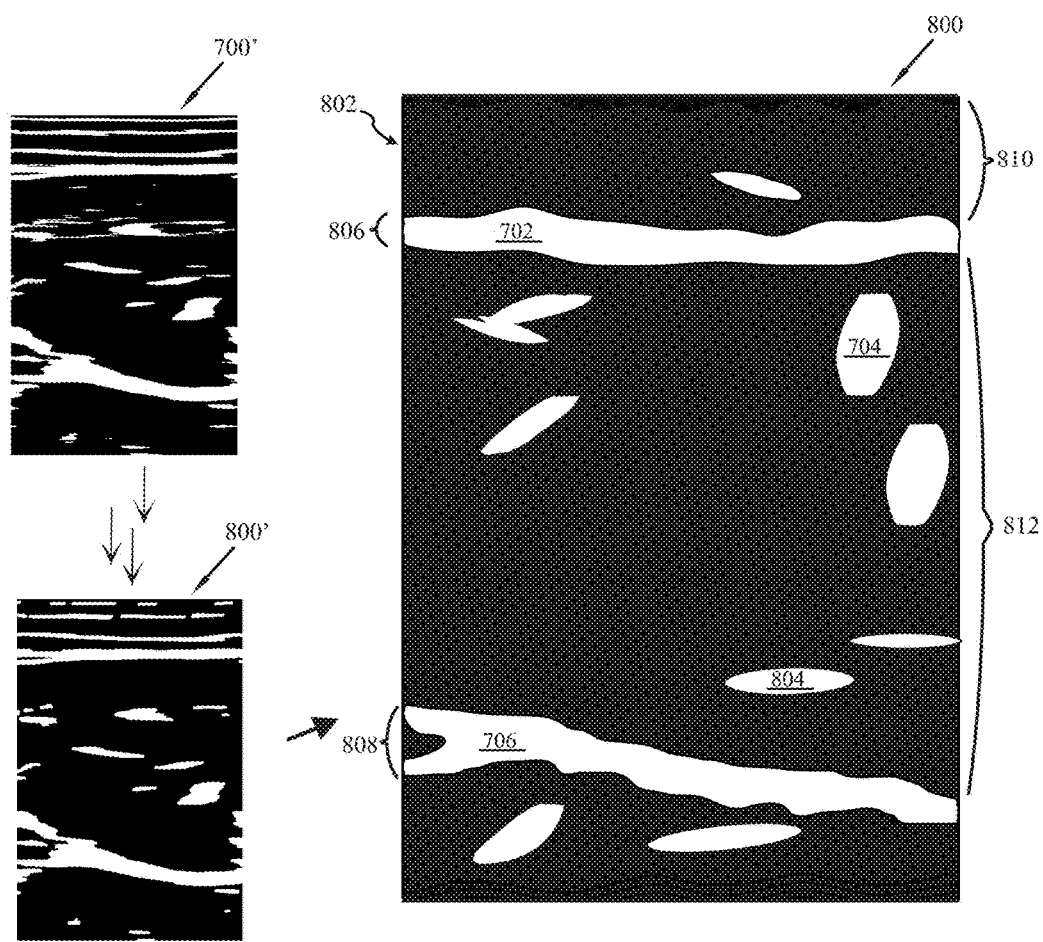
FIG. 8 is a conceptual illustration of a morphed image provided form the binary image in accordance with at least one embodiment.

More simply sated, for at least one embodiment the morphological function of opening is applied so as to further reduce the number of "white" elements within the binary image 700 so as to result in a reduced element image shown as morphed image 800, shown in FIG. 8. Again conceptual morphed image 800 corresponds generally to actual morphed image 800'.

Comparing morphed image 800 to binary image 700 it can and will be seen that the majority of smaller white elements, such as element 708 shown in FIG. 7, have been removed by the morphing process in providing morphed image 800.

With the elements of the processed binary image now further reduced it is quite clear that this morphed image 800 is distantly related to original scan image 200. However, because of the binary nature of morphed image 800 and the reduced number of elements, morphed image 800 is advantageously poised to permit the identification and distinguishing of a generally contiguous upper black element 802 within the morphed image 800, block 410.

For at least one embodiment, distinguishing the body fat layer as upper black element 802 from the remaining elements as asserted by block 410 is further understood and appreciated with respect to refinement 450. Moreover, an element such as exemplary element 804 is selected, block 452. For this selected element, one or more characteristics is determined, such as but not limited to area, center of mass, horizontal length, vertical height, etc. . . . . . It is understood and appreciated that the boundaries between different tissues is generally defined by fibrous tissues, which due to the above described image processing techniques have now evolved to being a generally continuous horizontal white band running generally continuously across the processed image.

Elements that do not have a horizontal length approaching the horizontal width of the processed image may generally be discounted and eliminated. Center of Mass and Area calculations may also be compared to reference expectations so as to further justify the elimination of all but the most likely bands defined by fibrous tissues.

Moreover, after determining one or more characteristics is determined for the selected element, method 450 continues with a query to determine if there are more elements remaining for analysis, decision 456. If there are indeed additional elements, a new element is elected, block 458 and the processes returns to determining one or more characteristics for the new element, block 454.

When all of the elements have been evaluated, and the non-fibrous tissue elements generally eliminated, there are in general two generally horizontal, generally continuous white bands, of which white bands 806, 808 are exemplary, to be appreciated within the processed image, block 460. There may indeed be several horizontal white bands that, but the image processing as described above has evolved the scan image to such an extent that there are at least two prominent white bands which both generally horizontal and generally continuous across the entire image. These prominent bands are readily distinguished over less prominent bands, such as by the calculations of center of mass, area, horizontal length and vertical height.

Because subcutaneous body fat, aka the adipose layer, is developed directly beneath the skin, the body fat layer 810 may be distinguished to be the top most black layer 802 which is above the top most generally horizontal and horizontally continuous band 806 with muscle tissue 812 generally being the tissue layer disposed there below. In other words the body fat layer 810 is distinguished to be the tissue layer 802 above the top most generally horizontal white band 806 that is generally horizontally continuous across the morphed image 800, block 462.

Figure 9:
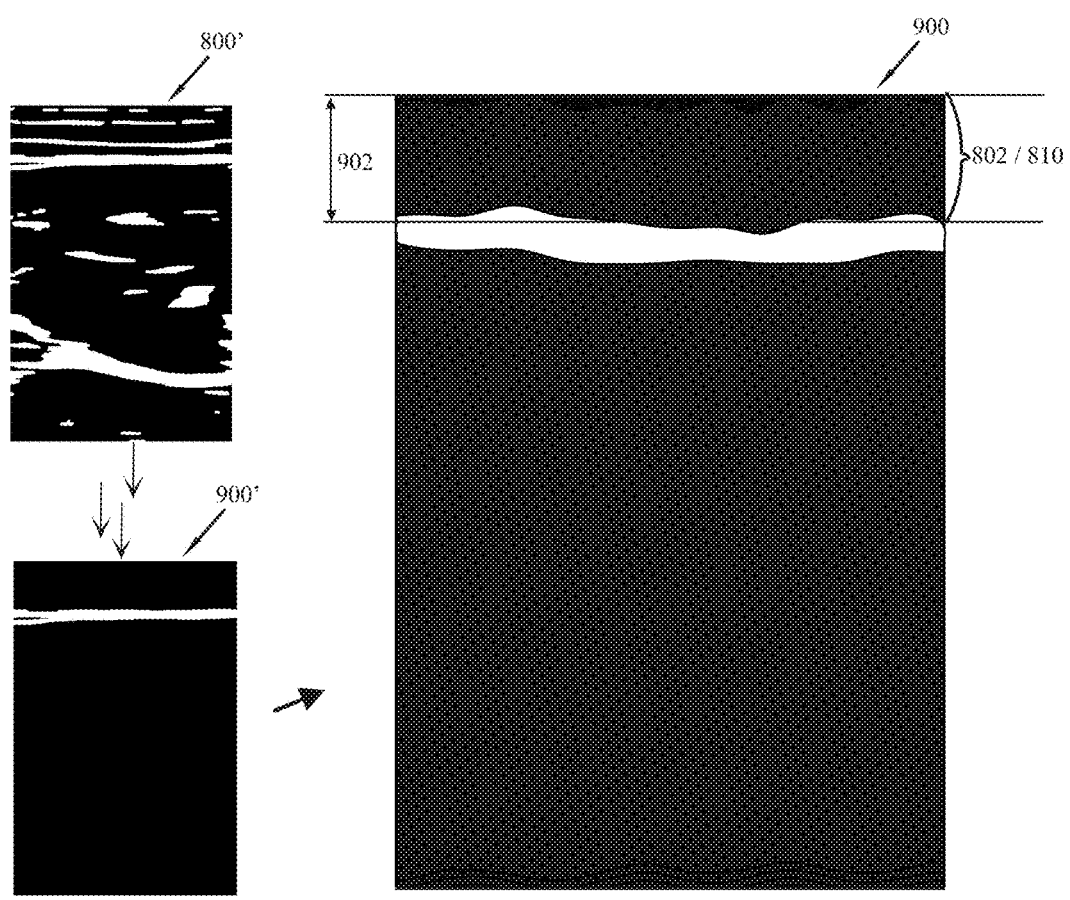
FIG. 9 is a conceptual illustration of the resulting processed image for non-invasive determination of human body fat in accordance with at least one embodiment.
Figure 10:
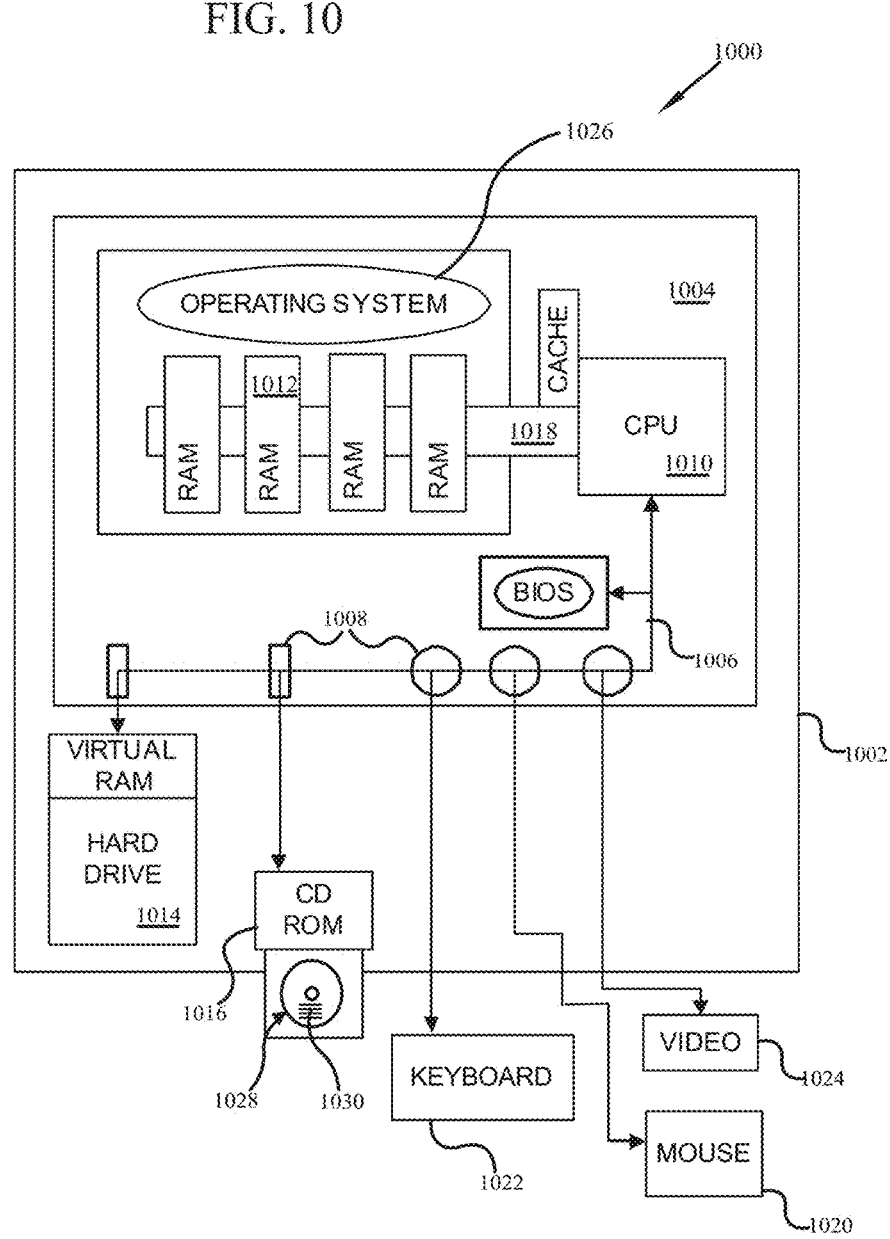
FIG. 10 is a block diagram of a computer system in accordance with at least one embodiment.

With the body fat layer now distinguished, the non-relevant layers may be further removed, for the resulting highly processed image 900 shown in FIG. 9. Once again, conceptual processed image 900 corresponds generally to actual processed image 900'.

As the scan image is known to have a scale, a determination of the thickness 902 for the distinguished body fat tissue layer 810 is now advantageously permitted with a high degree of precision, block 412. As shown, in FIG. 9, for at least one embodiment of the present invention, this determination of thickness 902 accounts for the average thickness of the distinguished body fat tissue layer 810 as identified in processed image 900. For varying alternative embodiments, the thickness 902 may be determined as the mean, median, mode or midrange value. Further still a combination of these values may be returned to the operator for potentially a greater understanding and appreciation of the subject's body fat tissue thickness as determined for one or more areas of his or her body.

To briefly summarize, for at least one embodiment the method of non-invasive determination of human body fat includes receiving at least one ultrasound scan image (block 302) of at least a portion of a skin layer as disposed above one or more additional tissue layers, the skin layer defining a horizontal axis and the image provided by a plurality of pixels; horizontally blurring the pixels of the image (block 404); thresholding the pixels of the image to provide a binary image having a plurality of elements of different sizes (block 406); morphing the structural elements of the binary image to remove small elements and connect large elements (block 408); distinguishing a body fat layer from the remaining elements (block 410); and determining the body fat layer thickness (412).

With the thickness of the body fat layer now determined, method 400 permits the operator to indicate whether or not it is desired to determine the scan image subject's body fat percentage, decision 414.

For some instances of application, such a determination of body fat percentage may not be desired, in which case method 400 may simply return the determined body fat layer thickness to the operator, block 416.

In other instances, such a determination of body fat percentage may indeed be desired. Because the body fat tissue layer has been distinguished and accurately measured for thickness, method 400 advantageously permits the application of well established skin fold equations as are often applied with respect to caliper measured body fat thickness, but without the potential for inadvertent caliper mismeasurement.

Moreover, it is generally accepted that for calculating a person's overall percentage of body fat a plurality of body fat thickness measurements should be obtained, such as from the abdominal, triceps, thigh and superaliac.

For an embodiment of SNDBT 100 and/or method 300 with refinement method 400 as performed with respect to the four body sites identified, the sum of the thickness is converted to millimeters, if not already in such units, and multiplied by two (2), block 418. This is because traditional skin fold measurements, actually measure a folded, and therefore stacked, set of body fat tissue layers. Of course, for at least one alternative embodiment, the sum of the thickness is not multiplied by two (2) before an equation is applied.

Skin fold equations are well known, and in varying embodiments for varying embodiments and genders, one or more skin fold equations may be selected and applied, block 420.

Moreover, the determined body fat value for a four (4) site skinfold equation as applied via SNDBT 100 and/or method 300 is as follows where T is the measured thickness in millimeters:

$$F=2\times(\text{abdominal } T+\text{triceps } T+\text{thigh } T+\text{superaliac } T)$$

For a male subject, in at least one embodiment the applied formula is then:

$$\% \text{ Body Fat}=(0.29288\times F)-(0.0005\times F^2)+(0.15845\times \text{Age})-2.76377$$

For a female subject, in at least one embodiment the applied formula is then:

$$\% \text{ Body Fat}=(0.29669\times F)-(0.00043\times F^2)+(0.02963\times \text{Age})+1.4072$$

(Formulas adapted from Jackson A S Pollack, M (1985) Practical Assessment of Body Composition. Physicians Sports Med. 13:76-90).

A three site equation may also be adopted for at least one alternative embodiment, such an equation being again adapted from the same Jackson A S Pollack reference:

$$\% \text{ Body Fat}=(0.41563\times F)-(0.00112\times F^2)+(0.03661\times \text{Age})+4.03653$$

With application of SNDBT 100 and/or method 300 the subject's skin is of course not actually being pinched or folded by mechanical means and therefore is not subject to the same shortcomings of a traditional caliper measurement. In addition, SNDBT 100 and/or method 300 advantageously permit the measurement and determination of body fat thickness in a variety of areas not previously suitable for caliper based measurement. By measuring these additional sites and comparing them with the more traditional sites, it is advantageously possible to establish a more specific profile for each individual being evaluated.

In addition, application SNDBT 100 and/or method 300 for the determination of body fat thickness is also applicable to other calculations such as body density.

For a male subject who has experienced a three site measurement via SNDBT 100 and/or method 300 with respect to the chest, abdomen and thigh, the male subject's body density is determined as follows:

$$D=2\times(\text{chest } T+\text{abdomen } T+\text{thigh } T)$$

$$\text{Density}=1.10938-(0.0008267\times D)+(0.0000016\times D^2)-(0.0002574\times \text{Age})$$

For a male subject who has experienced a seven site measurement via SNDBT 100 and/or method 300 with respect to the chest, axilla, tricep, subscapular, abdomen, superailiac and thigh, the male subject's body density is determined as follows:

$$D=2\times(\text{chest } T+\text{axilla } T+\text{tricep } T+\text{subscapular } T+\text{abdomen } T+\text{superailiac } T+\text{thigh } T)$$

$$\text{Density}=1.112-(0.00043499\times D)+(0.00000055\times D^2)-(0.00028826\times \text{Age})$$

Both male body density equations adapted from Jackson A S Pollack, M (1978), based on a sample aged 18-61.

For a female subject who has experienced a three site measurement via SNDBT 100 and/or method 300 with respect to the triceps, thigh and superailiac, the female subject's body density is determined as follows:

$$D=2\times(\text{triceps } T+\text{abdomen } T+\text{thigh } T)$$

$$\text{Density}=1.0994921-(0.0009929\times D)+(0.0000023\times D^2)-(0.0001392\times \text{Age})$$

For a female subject who has experienced a seven site measurement via SNDBT 100 and/or method 300 with respect to the chest, axilla, tricep, subscapular, abdomen, superailiac and thigh, the female subject's body density is determined as follows:

$$D=2\times(\text{chest } T+\text{axilla } T+\text{tricep } T+\text{subscapular } T+\text{abdomen } T+\text{superailiac } T+\text{thigh } T)$$

$$\text{Density}=1.112-(0.00046971\times D)+(0.00000056\times D^2)-(0.00012828\times \text{Age})$$

Both female body density equations adapted from Jackson A S Pollack, M (1978), based on a sample aged 18-61.

Moreover, the determination of body fat thickness as provided by SNDBT 100 and/or method 300 is applicable in a wide variety of qualified formulas for the determination of a number of different values which may be used by the subject or subject's doctor, trainer, care taker or other in a variety of different ways.

With respect to the above description of SNDBT 100 and methods 300, 350 and 400, it is understood and appreciated that the method may be rendered in a variety of different forms of code and instruction as may be preferred for different computer systems and environments. To expand upon the initial suggestion of a processor based device such as a computer 114 shown in FIG. 1 and discussed above, FIG. 10 is a high-level block diagram of an exemplary computer system 1000. Computer system 1000 has a case 1002, enclosing a main board 1004. The main board has a system bus 1006, connection ports 1008, a processing unit, such as Central Processing Unit (CPU) 1010 with at least one processor/microprocessor (not shown) and a memory storage device, such as main memory 1012, and optionally a solid state drive or hard drive 1014 and/or CD/DVD ROM drive 1016.

Memory bus 1018 couples main memory 1012 to CPU 1010. A system bus 1006 couples storage devices such as, but not limited to, hard drive 1014, CD/DVD ROM drive 1016 and connection ports 1008 to CPU 1010. Multiple input devices may be provided, such as for example a mouse 1020 and/or keyboard 1022. Multiple output devices may also be provided, such as for example a video display 1024 and a printer (not shown). In varying embodiments, the video display may also be a touch sensitive input device.

Computer system 1000 may be a commercially available system, such as a desktop workstation unit provided by IBM, Dell Computers, Gateway, Apple, Sun Micro Systems, or other computer system provider. Computer system 1000 may also be a smart phone or tablet computer such as an iPhone or iPad provided by Apple, the HP Slate, the Augen or Archos Android tablets, the Motorola Xoom or other such device. Computer system 1000 may also be a networked computer system, wherein memory storage components such as hard drive 1014, additional CPUs 1010 and output devices such as printers are provided by physically separate computer systems commonly connected together in the network. Those skilled in the art will understand and appreciate that physical composition of components and component interconnections comprising computer system 1000, and select a computer system 1200 suitable for the schedules to be established and maintained.

When computer system 1000 is activated, preferably an operating system 1026 will load into main memory 1012 as part of the boot strap startup sequence and ready the computer system 1000 for operation. At the simplest level, and in the most general sense, the tasks of an operating system fall into specific categories—process management, device management (including application and user interface management) and memory management.

In such a computer system 1000, the CPU 1010 is operable to perform one or more of the methods of non-invasive determination of glycogen stores as described above. Those skilled in the art will understand that a computer-readable medium 1028 on which is a computer program 1430 for non-invasive determination of glycogen stores may be provided to the computer system 1000. The form of the medium 1028 and language of the program 1030 are understood to be appropriate for computer system 1000. Utilizing the memory stores, such as for example one or more hard drives 1014 and main system memory 1012, the operable CPU 1002 will read the instructions provided by the computer program 1030 and operate to perform as SNDBT 100 as described above.

To summarize, for at least one embodiment, a system for non-invasive system of determining human body fat is provided by a processing unit; a memory storage device coupled to the processing unit; the processing unit being adapted to: receive at least one ultrasound scan image of at least a portion of a skin layer as disposed above one or more additional tissue layers, the skin layer defining a horizontal axis and the image provided by a plurality of pixels; horizontally blur the pixels of the image; threshold the pixels of the image to provide a binary image having a plurality of elements of different sizes; morph the structural elements of the binary image to remove small elements and connect large elements; distinguish a body fat layer from the remaining elements; and determine the body fat layer thickness.

Figure 11:
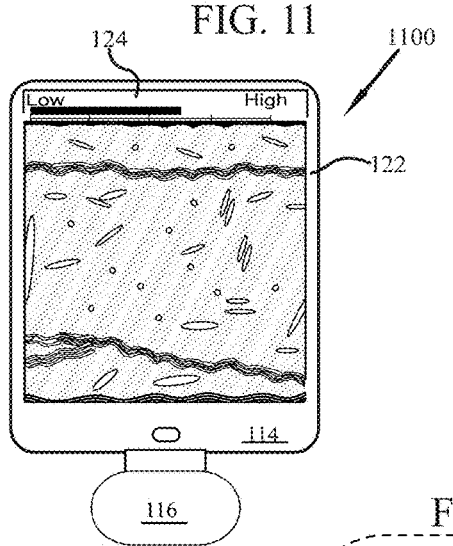
FIGS. 11-13 are conceptual illustrations of alternative configurations for a system for non-invasive determination of glycogen stores in accordance with at least one embodiment.
Figure 12:
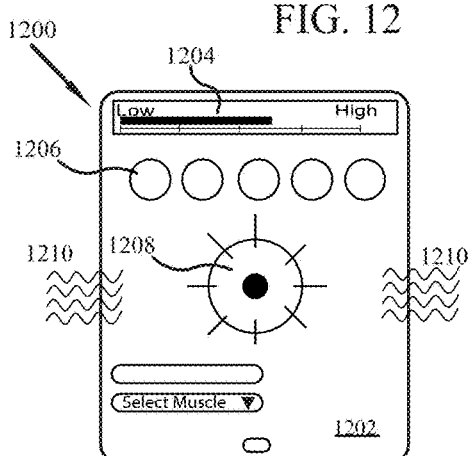
Figure 13:
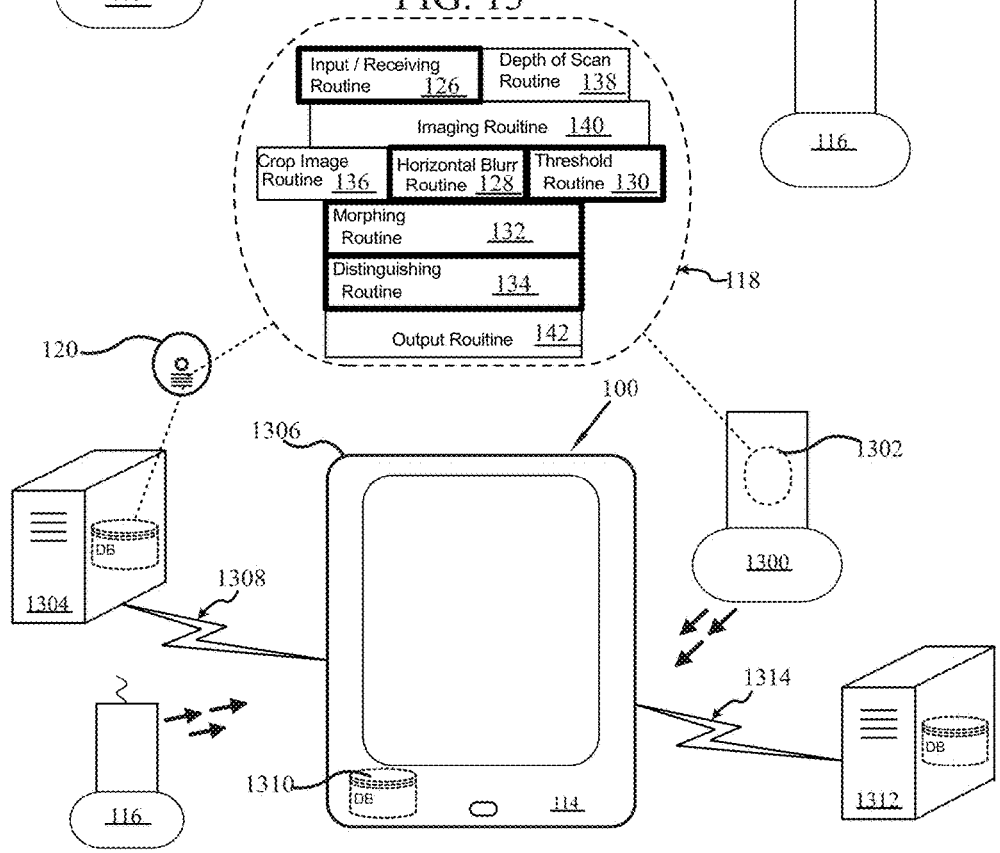

With respect to the various forms of the processor based device, such as the computer 114, further discussed and described as computer 1000, FIGS. 11-13 presents alternative embodiments for the structural arrangement of components comprising SNDBT 100. More specifically, for alternative SNDBT 1500 as shown in FIG. 11, the ultrasound transducer 116 is coupled directly to the computer 114, such that SNDBT 1100 is itself disposed adjacent to the target tissue 108 (not shown).

For alternative SNDBT 1200 shown as FIG. 12, a dedicated processor based device such as a customized computer 1202 is provided, as opposed to adapting a pre-existing smart phone, tablet computer or other computer system. For SNDBT 1200, the display 122 of SNDBT 1200 is not shown so as to illustrate that alternative output devices such as an indicator 1204, lights 1206, speaker 1208, vibrator 1210 and/or combinations thereof can provide an operator with an indication of the non-invasively determined glycogen store. As with SNDBT 1100, the ultrasound transducer 116 may be directly coupled to the customized computer 1202, or tethered by a communications link 1212—wireless or wired as shown.

Further, for yet other embodiments, the computer program 118 to adapt a computer 114 may be provided directly by enhanced ultrasound transducer 1300. More specifically, computer program 118 may be incorporated as part of the circuit structure 1302 of enhanced ultrasound transducer 1300 such that upon connection to computer 114, SNDBT 100 is provided.

As suggested above with respect to FIG. 1, the computer program 118 may also be provided by a non-portable media such as a disc 120 to a third party computer, such as computer 1304, providing an application platform such as but not limited to the Apple App Store. A user can then connect his or her computer 114, such as tablet computer 1306 to the third party computer 1304 by a network 1308 (wired or wireless) or other communication channel and obtain computer program 118 so as to adapt his or her computer 1306 to perform as SNDBT 100 when a scan of a target muscle is provided.

In varying embodiments, this scan may be provided by coupling computer 1306 to ultrasound transducer 116 operated as described above, receiving a scan of a target muscle from internal storage 1310, or receiving a scan of a target muscle another computer system 1312 via wired or wireless network 1314, or other appropriate communication channel.

To summarize, for at least one embodiment, the present invention is provided upon a non-transitory machine readable medium on which is stored a computer program comprising instructions to adapt a computer system having a processor to permit non-invasive determination of human body fat. This computer program includes computer executable instructions to provide a receiving routine operatively associated with an input device for receiving at least one ultrasound scan image of at least a portion of a skin layer as disposed above one or more additional tissue layers, the skin layer defining a horizontal axis and the image provided by a plurality of pixels; a horizontal blurring routine for horizontally blurring the pixels of the image; a thresholding routine for thresholding the pixels of the image to provide a binary image having a plurality of elements of different sizes; a morphing routine for morphing the structural elements of the binary image to remove small elements and connect large elements; and a distinguishing routine for distinguishing a body fat layer from the remaining elements and determining the body fat layer thickness.

Changes may be made in the above methods, systems and structures without departing from the scope hereof. It should thus be noted that the matter contained in the above description and/or shown in the accompanying drawings should be interpreted as illustrative and not in a limiting sense. The following claims are intended to cover all generic and specific features described herein, as well as all statements of the scope of the present method, system and structure, which, as a matter of language, might be said to fall therebetween.

What is claimed is:

1. A non-invasive method of determining human body fat, comprising:
   receiving at least one ultrasound scan image of at least a portion of a skin layer as disposed above one or more additional tissue layers, the skin layer defining a horizontal axis and the image provided by a plurality of pixels;
   horizontally blurring the pixels of the image;
   thresholding the pixels of the image to provide a binary image having a plurality of elements of different sizes;
   morphing the structural elements of the binary image to remove small elements and connect large elements;
   distinguishing a body fat layer from the remaining elements; and
   determining the body fat layer thickness.

2. The method of claim 1, wherein the percentage of body fat is determined by multiplying the determined body fat layer thickness by 2 and applying a skin fold equation.

3. The method of claim 1, wherein the morphing is mathematical morphology.

4. The method of claim 1, wherein the morphing includes applying a morphological function for opening.

5. The method of claim 1, wherein distinguishing the body fat layer further includes evaluating at least a subset of the remaining elements.

6. The method of claim 5, wherein evaluating at least a subset of the remaining elements includes determining, for each element, one or more characteristics selected from the group consisting of: area, center of mass, and horizontal length.

7. The method of claim 5, wherein the body fat layer is distinguished to be a tissue layer above a top most generally horizontal white band that is generally horizontally continuous across the binary image.

8. The method of claim 1, further comprising imaging a selected portion of a subject's body with an ultrasound device having a movable transducer to provide the ultrasound scan image.

9. The method of claim 1, wherein the determination of body fat is performed about contemporaneously with the imaging of the subject with the ultrasound device for another purpose.

10. The method of claim 1, further comprising vertically cropping one or both sides of the image before horizontally blurring the remaining central portion of the image.

11. The method of claim 10, wherein between $1/10$ and $1/5$ of the image is vertically cropped from one or both sides.

12. The method of claim 1, wherein the method is repeated over time upon additional scan images to evaluate the body fat layer over time.

13. The method of claim 1, wherein the method is about contemporaneously performed on different scan images from different locations about a subject's body.

14. A non-invasive method of determining human body fat, comprising:
   providing an ultrasound device having a movable transducer, the transducer operable in a high frequency range;
   selecting a target area of a subject;
   adjusting the ultrasound device for a depth of scan appropriate for the selected target area;
   disposing the transducer proximate to the subject and perpendicular to the selected target area;
   scanning the selected target area by processing ultrasound reflection received by the transducer to provide at least a partial scan image of the selected target area, the image provided by a plurality of pixels; horizontally blurring the pixels of the image;
   thresholding the pixels of the image to provide a binary image having a plurality of elements of different sizes;
   morphing the structural elements of the binary image to remove small elements and connect large elements;
   distinguishing a body fat layer from the remaining elements; and
   determining the body fat layer thickness.

15. The method of claim 14, wherein the percentage of body fat is determined by multiplying the determined body fat layer thickness by 2 and applying a skin fold equation.

16. The method of claim 14, wherein the morphing is mathematical morphology.

17. The method of claim 14, wherein the morphing includes applying a morphological function for opening.

18. The method of claim 14, wherein distinguishing the body fat layer further includes evaluating at least a subset of the remaining elements.

19. The method of claim 18, wherein evaluating at least a subset of the remaining elements includes determining, for each element, one or more characteristics selected from the group consisting of: area, center of mass, and horizontal length.

20. The method of claim 18, wherein the body fat layer is distinguished to be a tissue layer above a top most generally horizontal white band that is generally horizontally continuous across the binary image.

21. The method of claim 14, further comprising vertically cropping one or both sides of the image before horizontally blurring the remaining central portion of the image.

22. The method of claim 21, wherein between $1/10$ and $1/5$ of the image is vertically cropped from one or both sides.

23. The method of claim 14, wherein the method is repeated over time upon additional scan images to evaluate the body fat layer over time.

24. The method of claim 14, wherein the method is performed in about real time.

25. A non-invasive system of determining human body fat, comprising:
   a processing unit;
   a memory storage device coupled to the processing unit;
   the processing unit being adapted to:

receive at least one ultrasound scan image of at least a portion of a skin layer as disposed above one or more additional tissue layers, the skin layer defining a horizontal axis and the image provided by a plurality of pixels;

horizontally blur the pixels of the image;

threshold the pixels of the image to provide a binary image having a plurality of elements of different sizes;

morph the structural elements of the binary image to remove small elements and connect large elements;

distinguish a body fat layer from the remaining elements; and determine the body fat layer thickness.

26. The non-invasive system of claim 25, wherein the percentage of body fat is determined by multiplying the determined body fat layer thickness by 2 and applying a skin fold equation.

27. The non-invasive system of claim 25, wherein the morphing is mathematical morphology.

28. The non-invasive system of claim 25, wherein the morphing includes applying a morphological function for opening.

29. The non-invasive system of claim 25, wherein distinguishing the body fat layer further includes evaluating at least a subset of the remaining elements.

30. The non-invasive system of claim 29, wherein evaluating at least a subset of the remaining elements includes determining, for each element, one or more characteristics selected from the group consisting of: area, center of mass, and horizontal length.

31. The non-invasive system of claim 29, wherein the body fat layer is distinguished to be a tissue layer above a top most generally horizontal white band that is generally horizontally continuous across the binary image.

32. The non-invasive system of claim 25, further including an ultrasound device having a movable transducer, the transducer operable in a high frequency range, the ultrasound device coupled to the processing unit.

33. The non-invasive system of claim 25, further comprising vertically cropping one or both sides of the image before horizontally blurring the remaining central portion of the image.

34. The non-invasive system of claim 33, wherein between 1/10 and 1/5 of the image is vertically cropped from one or both sides.

35. The non-invasive system of claim 25, wherein the method is repeated over time upon additional scan images to evaluate the body fat layer over time.

36. A non-transitory machine readable medium on which is stored a computer program comprising instructions to adapt a computer system having a processor to permit non-invasive determination of human body fat, the computer program comprising:

a receiving routine operatively associated with an input device for receiving at least one ultrasound scan image of at least a portion of a skin layer as disposed above one or more additional tissue layers, the skin layer defining a horizontal axis and the image provided by a plurality of pixels;

a horizontal blurring routine for horizontally blurring the pixels of the image;

a thresholding routine for thresholding the pixels of the image to provide a binary image having a plurality of elements of different sizes;

a morphing routine for morphing the structural elements of the binary image to remove small elements and connect large elements; and a distinguishing routine for distinguishing a body fat layer from the remaining elements and determining the body fat layer thickness.

37. The non-transitory machine readable medium of claim 36, wherein the percentage of body fat is determined by multiplying the determined body fat layer thickness by 2 and applying a skin fold equation.

38. The non-transitory machine readable medium of claim 36, wherein the morphing routine applies mathematical morphology.

39. The non-transitory machine readable medium of claim 36, wherein distinguishing the body fat layer further includes evaluating at least a subset of the remaining elements.

40. The non-transitory machine readable medium of claim 39, wherein evaluating at least a subset of the remaining elements includes determining, for each element, one or more characteristics selected from the group consisting of: area, center of mass, and horizontal length.

41. The non-transitory machine readable medium of claim 39, wherein the body fat layer is distinguished to be a tissue layer above a top most generally horizontal white band that is generally horizontally continuous across the image.

42. The non-transitory machine readable medium of claim 36, further comprising imaging a selected portion of a subject's body with an ultrasound device having a movable transducer to provide the ultrasound scan image.

43. The non-transitory machine readable medium of claim 36, further including a crop image routine for vertically cropping one or both sides of the image before horizontally blurring the remaining central portion of the image.

44. The non-transitory machine readable medium of claim 43, wherein between 1/10 and 1/5 of the image is vertically cropped from one or both sides.

45. The non-transitory machine readable medium of claim 36, wherein the non-invasive determination of human body fat is repeated over time upon additional scan images to evaluate the body fat layer over time.

46. The non-transitory machine readable medium of claim 36, wherein the non-invasive determination of human body fat is about contemporaneously performed on different scan images from different locations about a subject's body.

\* \* \* \* \*